(12) United States Patent
Tornier

(10) Patent No.: US 6,761,740 B2
(45) Date of Patent: Jul. 13, 2004

(54) GLENOID COMPONENT OF A SHOULDER PROSTHESIS AND COMPLETE SHOULDER PROSTHESIS INCORPORATING SUCH A COMPONENT

(75) Inventor: Alain Tornier, Saint Ismier (FR)

(73) Assignee: Tornier, Saint Ismier (FR)

( * ) Notice: Subject to any disclaimer, the term of this patent is extended or adjusted under 35 U.S.C. 154(b) by 0 days.

(21) Appl. No.: 10/364,681

(22) Filed: Feb. 12, 2003

(65) Prior Publication Data

US 2003/0158605 A1 Aug. 21, 2003

(30) Foreign Application Priority Data

Feb. 15, 2002 (FR) .............................. 02 01944

(51) Int. Cl.$^7$ .............................. A61F 2/40; A61F 2/30
(52) U.S. Cl. .................... 623/19.13; 623/23.4
(58) Field of Search .................... 623/16.11, 18.11, 623/19.11–19.14, 23.39, 23.4

(56) References Cited

U.S. PATENT DOCUMENTS 3,978,528 A      9/1976    Crep 5,462,563 A  *  10/1995   Shearer et al. ................ 623/18

FOREIGN PATENT DOCUMENTS

| DE | 19548154 | 6/1997 | |
|----|----------|--------|---|
| EP | 0953321  | 11/1999 | |
| FR | 2652498  | 4/1991 | |
| FR | 2704747  | 11/1994 | |
| GB | 2297257  | * 7/1996 | ............. A61F/2/40 |

* cited by examiner

Primary Examiner—Eduardo C. Robert
Assistant Examiner—Anuradha Ramana
(74) Attorney, Agent, or Firm—Dowell & Dowell, P.C.

(57) ABSTRACT

A shoulder prosthesis glenoid component which includes a base adapted to be immobilized on a glenoid cavity of a shoulder, and an element including a convex articulation surface adapted to cooperate with a humeral component of the prosthesis. The element is selectively mounted on the base in a plurality of positions corresponding to different positions of the convex articulation surface with respect to the glenoid cavity.

10 Claims, 4 Drawing Sheets

GLENOID COMPONENT OF A SHOULDER PROSTHESIS AND COMPLETE SHOULDER PROSTHESIS INCORPORATING SUCH A COMPONENT

BACKGROUND OF THE INVENTION

The present invention relates to a glenoid component for a shoulder prosthesis and to a complete shoulder prosthesis incorporating such a component.

BRIEF DESCRIPTION OF THE RELATED ART

In the domain of shoulder prostheses, it is known, for example from U.S. Pat. No. 3,978,528, to constitute an inverted prosthesis in which a convex articular surface is secured to the glenoid cavity, while a concave articular surface is secured to the humerus, the cooperation of these surfaces making it possible to re-create a joint of the shoulder. In this type of prosthesis, a base may be used which is fixed on the glenoid cavity and on which is mounted an element forming the convex articulation surface.

The design of inverted prostheses of the type mentioned above responds to the need to restore the indolence and the function of the shoulder joint in the cases of massive destruction of the cover of the elements ensuring rotation. In that case, the raising of the arm is ensured solely by the deltoid muscle. It is therefore important that the lever arms corresponding to the points of application of the forces undergone by the joint be determined with high precision in order to limit as much as possible the efforts that a patient must develop in order to raise an arm fitted with a shoulder prosthesis. In effect, the known prostheses sometimes cause discomfort for the patients.

It is a more particular object of the present invention to overcome these drawbacks by proposing a glenoid component of a shoulder prosthesis which takes maximum advantage of the muscular tension, reducing the efforts necessary for raising the arm.

SUMMARY OF THE INVENTION

In this spirit, the invention relates to a glenoid component of a shoulder prosthesis which comprises a base, adapted to be immobilized on the glenoid cavity of a shoulder, and an element forming a convex articulation surface adapted to cooperate with a humeral component of the prosthesis, this element being provided to be mounted on this base. This component is characterized in that the element forming the convex surface is adapted to be mounted on the base in a plurality of positions corresponding respectively to different positions of the convex articulation surface with respect to the glenoid cavity.

Thanks to the invention, the different possible positions of the convex articulation surface with respect to the glenoid cavity may be used for varying, in pre-operatory phase, the position of this surface, which makes it possible to adjust with precision the geometry of the joint thus re-created.

According to advantageous but non-obligatory aspects of the invention, this component incorporates one or more of the following characteristics:

The element forming an articulation surface is constituted by a piece in the form of a portion of sphere forming the articulation surface and by a plate adapted to support this piece and provided with means for positioning and fixation with respect to the base.

Means are provided for indexation of the position of the element forming the convex articulation surface with respect to the base. These indexation means, i.e. for incremental positioning, may comprise an extension projecting from the afore-mentioned element, as well as a plurality of housings provided on the base for the selective reception of this extension. Depending on the housing in which the afore-mentioned extension is received, different positions of the convex articulation surface with respect to the glenoid cavity are obtained. The afore-mentioned housings are advantageously defined by the edges of a notch made in a web of the base intended to be applied against the glenoid cavity. In addition, the indexation means may be provided to comprise orifices for passage of screws kinematically linked to the element forming the convex articulation surface, these orifices being distributed in the vicinity of the afore-mentioned housings in order to receive these screws, as a function of the position of the extension in one of these housings.

When the element forming the extension is bipartite as indicated hereinabove, the extension that it comprises may be hollow and form a passage for a screw for fixing the piece in the form of a portion of sphere on the plate.

The different positions of the element forming the convex articulation surface with respect to the ground are three in number and are offset, in the sagittal plane, by about 5 mm with respect to one another.

The base is provided with an acromio-coracoid bearing flange which extends substantially in a direction perpendicular to a web of the base in which are provided means for assembly of the element forming the convex articulation surface.

The invention also relates to a complete shoulder prosthesis which comprises a glenoid component as described hereinabove. Such a prosthesis is more comfortable for the patient than the known inverted prostheses.

BRIEF DESCRIPTION OF THE DRAWINGS

The invention will be more readily understood on reading the following description of a glenoid component and of a prosthesis in accordance with its principle, given solely by way of example and made with reference to the accompanying drawings, in which.

DESCRIPTION OF PREFERRED EMBODIMENT

Figure 1:
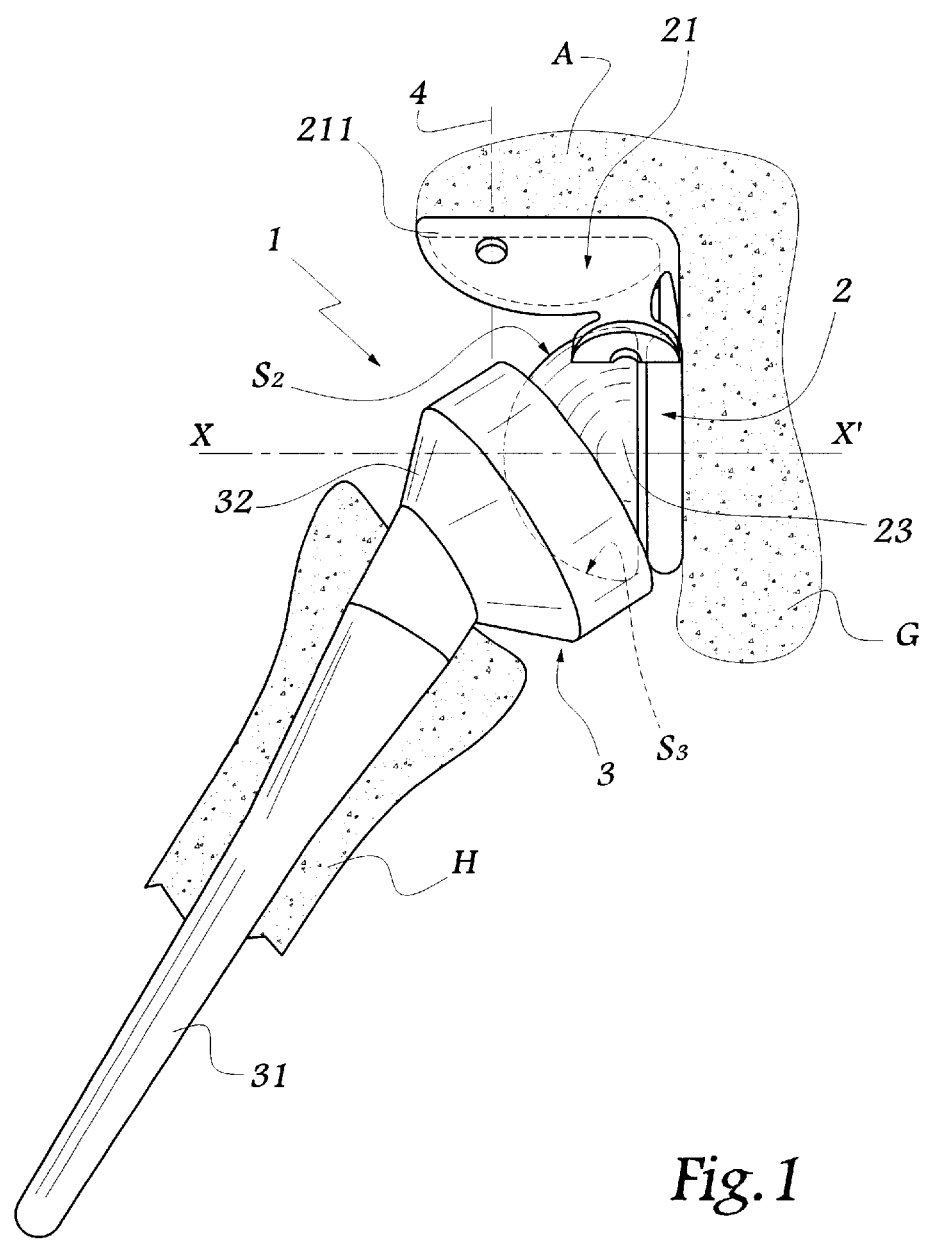
FIG. 1 schematically shows a prosthesis according to the invention, implanted on a patient.

Referring now to the drawings, the prosthesis 1 shown in FIG. 1 comprises a first component 2 fixed on the glenoid cavity G of a shoulder, as well as a second component 3 fixed in the corresponding humerus H.

The component 3 comprises a stem 31 intended to be anchored in the intermedullary canal of the humerus H. The component 3 also comprises a part 32 defining a concave surface $S_3$ in the form of a portion of sphere.

Figure 3:
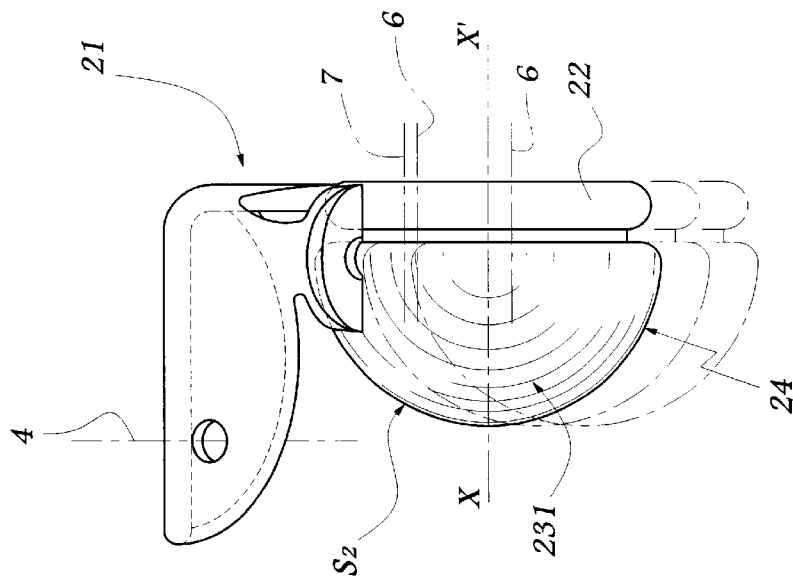
FIG. 3 is a side view of the component of FIG. 2.
Figure 2:
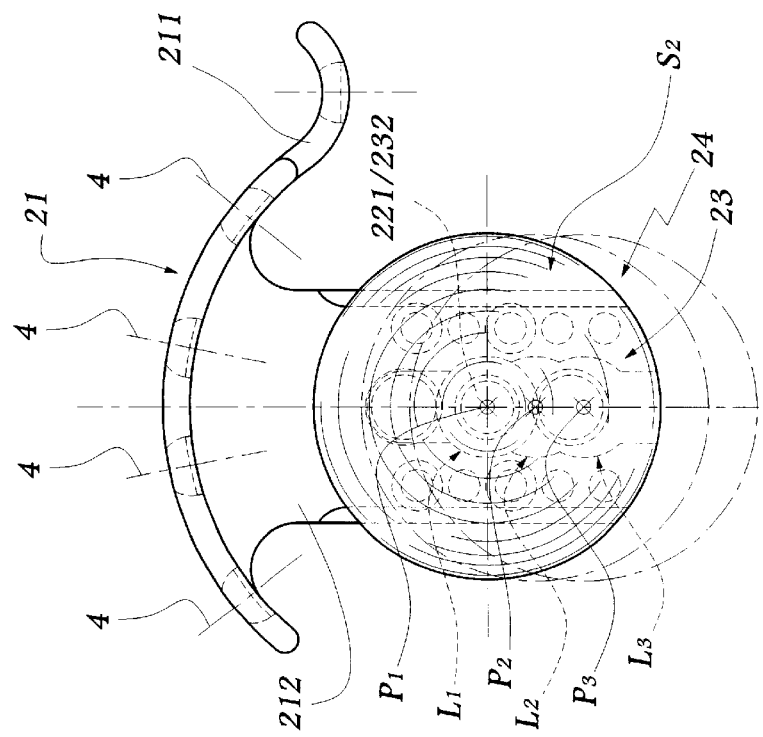
FIG. 2 is a front view, in the direction of arrow $F_1$ in FIG. 1, of the glenoid component of the prosthesis of FIG. 1.
Figures 4, 5:
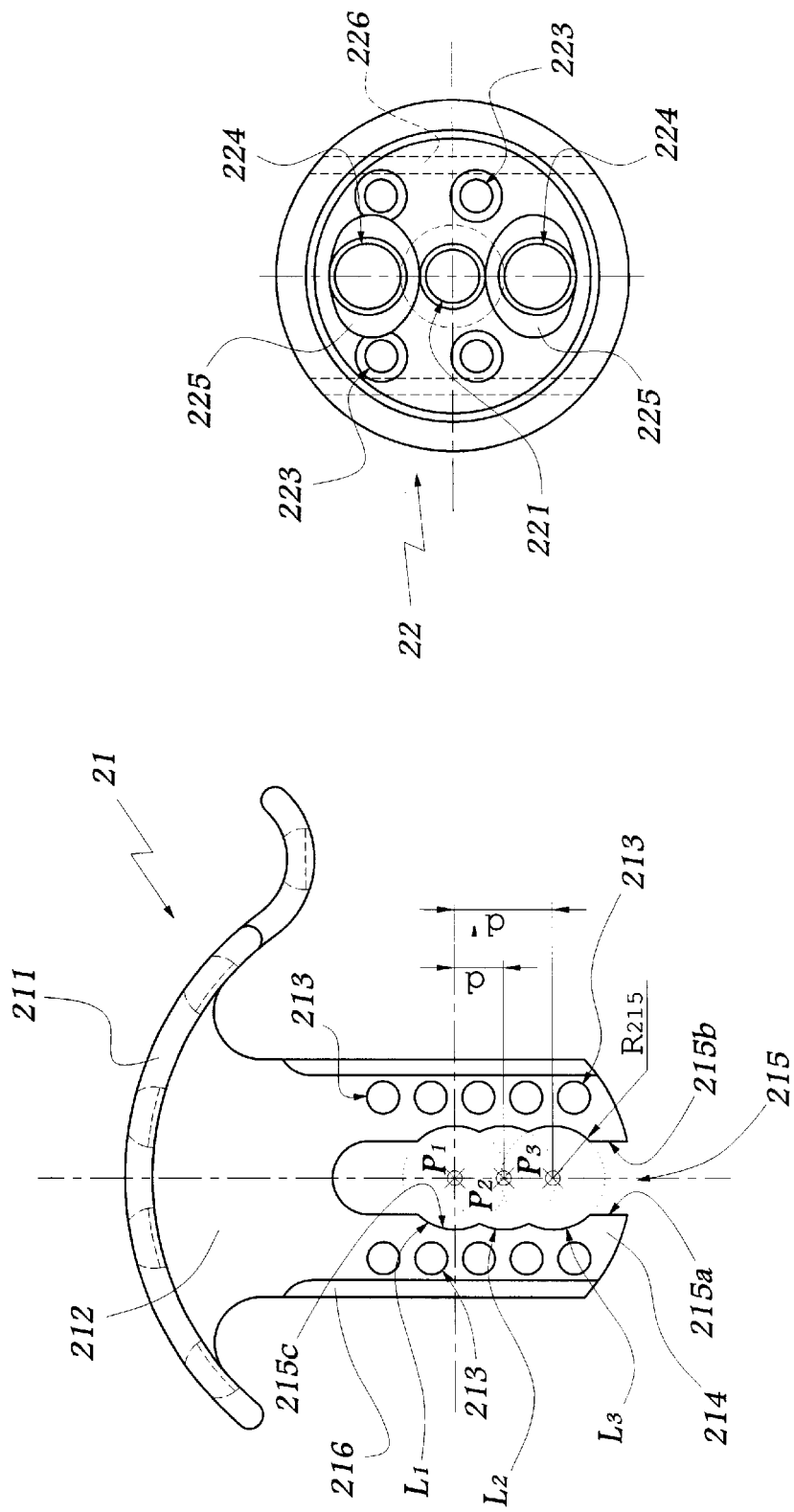
FIG. 4 is a front view of a base belonging to the component of FIGS. 2 and 3.
FIG. 5 is a front view of a plate belonging to the component of FIGS. 2 and 3.
Figure 6:
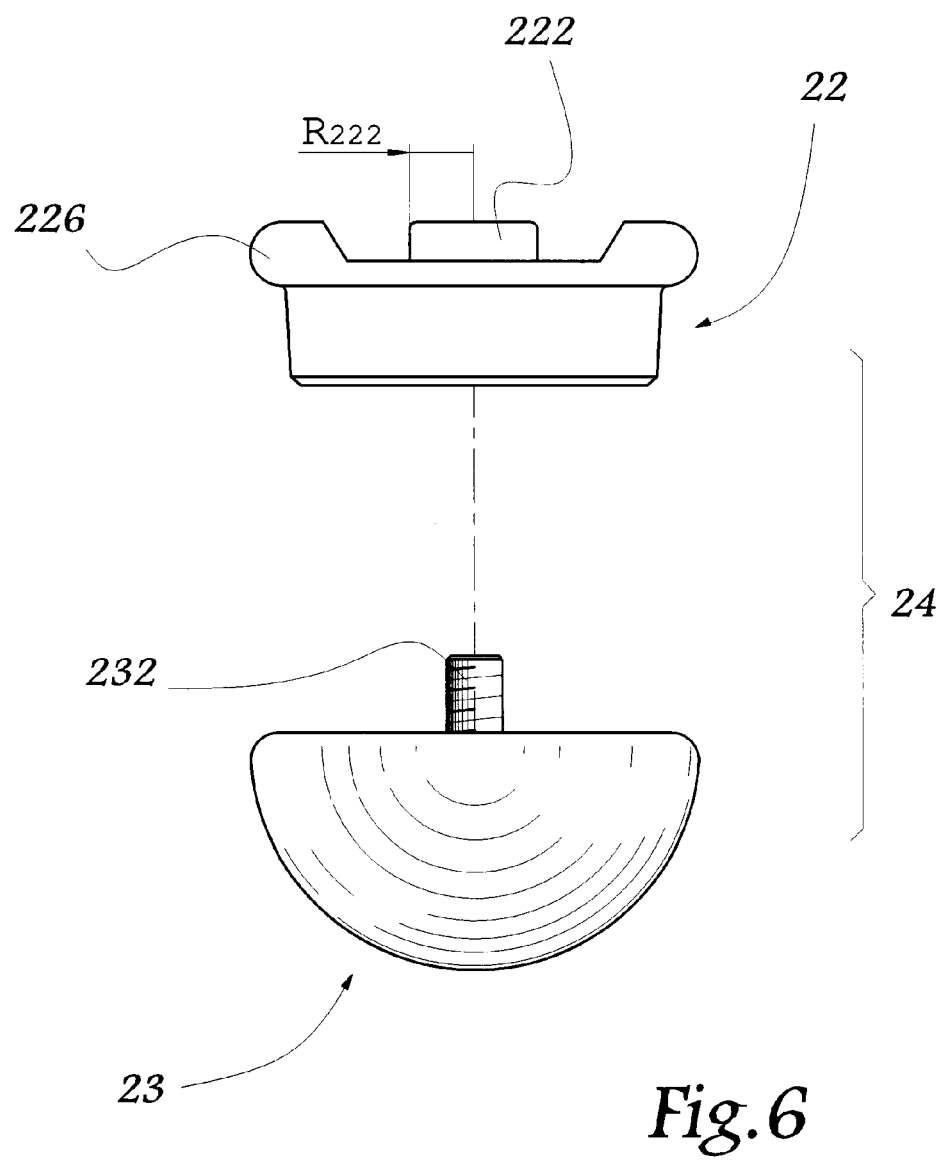
FIG. 6 is an exploded view of an element forming a convex articulation surface, comprising the plate of FIG. 5 and intended to cooperate with the base of FIG. 4 in order to constitute the component of FIGS. 2 and 3.

The component 2 comprises a base 21 provided to be immobilized on the acromion A thanks to screws 4 traversing a flange 211 of the base 21 intended to come into abutment against the acromion. This flange 211 is of curved shape and extends substantially perpendicularly to a web 212 of the base 21 more particularly visible in FIG. 4. In FIGS. 1 to 3, the traces of the screws 4 have been represented by axis lines in order to render the drawings clearer.

The flange 211 is optional and the base 21 may be fixed on the glenoid cavity by any appropriate means.

The component 2 also comprises a metal plate 22 intended to be associated with a metal piece 23 of which the outer surface 231 constitutes a convex or partial spherical articulation surface $S_2$ which cooperatively seats with the afore-mentioned surface $S_3$.

The plate 22 and the piece 23 are assembled thanks to a screw 232 secured to piece 23 and adapted to engage in an orifice 221 made in the central part of the plate 22, inside a circular-base cylindrical extension 222, which is hollow in order to constitute the orifice 221. The orifice 221 is tapped over at least a part of its length in order to cooperate with the screw 232.

The web 212 is provided with a plurality of bores 213 made in two flanges 214 formed on either side of a notch 215 made in the web 212. The longitudinal edges 215a and 215b of this notch each form three arcuate sectors 215c centred on three imaginary points $P_1$, $P_2$ and $P_3$ and of which the radius $R_{215}$ is substantially equal to the radius $R_{222}$ of the extension 222.

In this way, the plate 22 may be applied against the web 212 of the base 21 in three positions corresponding respectively to the engagement of the extension 222 in each of the three housings $L_1$, $L_2$, $L_3$ formed by the notch 215 around each of the points $P_1$, $P_2$ and $P_3$.

The housing $L_1$ is such that, if the extension 222 is engaged in this housing, the geometric centre $C_2$ of the surface $S_2$ is substantially aligned with a median axis X–X' passing through the geometric centre of the glenoid pyramid in the frontal plane.

The distance d between the points $P_1$ and $P_2$ is equal to about 5 mm, similarly to the distance d' between points $P_2$ and $P_3$. It is therefore possible to obtain, from the position of the surface $S_2$ shown in solid lines in FIGS. 2 and 3, which position corresponds to the introduction of the extension 222 in the housing $L_1$, two positions of downwardly vertical offset in the sagittal plane which respectively correspond to displacements of 5 and 10 mm, in the sagittal plane and downwards. These second and third positions, which respectively correspond to the positioning of the extension 222 in the housing $L_2$ and in the housing $L_3$, are represented in dashed and dotted lines in FIGS. 2 and 3.

When the position of the plate 22 with respect to the base 21 has been determined, this position is fixed by the introduction, into four orifices 223 provided on the plate 22, of screws 6 intended to penetrate into certain of the bores 213. The screws in question are represented by their axis lines 6 in FIG. 3.

The bores 213 may be tapped, in which case the screws 6 engage therein. The bores 213 may also be smooth, in which case the screws 6 are directly screwed in the glenoid cavity.

Furthermore, two orifices 224 are provided in the plate 22, which are disposed on either side of the orifice 221 and provided for the passage of screws for fixing the plate 22 with respect to the glenoid cavity G. These screws are represented by their axis line 7 in FIGS. 2 and 3 and they present diameters larger than the screws 6. The screws 7 penetrate into the glenoid cavity G, traversing the notch 215.

The plate 22 forms, around the orifices 224, seats 225 of rounded and concave shape adapted to cooperate with the heads of the screws 7, so that the screws 7 may have different orientations with respect to the web 212, this making it possible to select that part of the glenoid cavity G in which the screws 7 are implanted, as desired.

The plate 22 is provided with two returns 226 provided to overlap the longitudinal edges 216 of the web 212.

Thanks to the screws 6 and 7, it is therefore possible to immobilize the surface $S_2$ with respect to the base 21 in one of the three configurations respectively represented in solid lines and in dashed and dotted lines in FIGS. 2 and 3.

The three possible positions of the element 24, formed by the plate 22 and the piece 23, with respect to the base 21 correspond to the superposition of the centre of plate 22 with one of the points $P_1$, $P_2$ or $P_3$.

The component 2 is placed in position by firstly positioning the base 21 and by fixing it on the acromion thanks to screws 4. Thanks to phantom elements which reproduce the shape of the surface $S_2$, the surgeon can then make trial positionings and choose the position most adapted for the element formed by the plate 22 and the piece 23. Once this position is chosen, the plate 22 is connected to the base 21 and the whole is fixed to the glenoid cavity G by screws 7. The partially spherical piece 23 is then impacted on the plate and immobilized thereon thanks to screws 6.

According to a variant embodiment of the invention (not shown), the position of the surface $S_2$ with respect to the base 21 may also be adjusted in an antero-posterior direction, i.e. towards the left or towards the right in FIG. 2. In that case, the geometry of the housings provided on the base 21 is adapted accordingly.

What is claimed is:

1. A glenoid component for a shoulder prosthesis having a humeral component with a concave articulation surface, the glenoid component including a base adapted to be immobilized on a glenoid cavity of a shoulder and an element including a convex articulation surface adapted to cooperate with the concave articulation surface of the humeral component of the prosthesis, and means for adjustable mounting said element to said base such that said convex articulation surface is selectively positioned with respect to the glenoid cavity.

2. The component of claim 1, wherein said element is constituted by a piece in a form of a portion of a sphere forming said convex articulation surface and by a plate supporting said piece, and said means for adjustable mounting including means for positioning and securing said element in one of a plurality of different positions with respect to said base.

3. The component of claim 2, wherein said means for positioning and securing includes an extension projecting from said element, and a plurality of housings provided on said base for selective reception of said extension and said extension being hollow and forming a passage for a screw for securing said piece on said plate.

4. The component of claim 1, wherein said means for adjustably mounting includes means for indexing said element to different positions with respect to said base.

5. The component of claim 4, wherein said means for indexing comprises an extension projecting from said element, and a plurality of housings provided on said base for selective reception of said extension.

6. The component of claim 5, wherein said housings are defined by opposing edges of a notch made in a web of said base, which web is adapted to be applied against the glenoid cavity.

7. The component of claim 5, wherein said means for indexing comprises orifices for passage of screws kinematically linked to said element, said orifices being distributed in a vicinity of the housings to receive said screws as a function of a position of said extension in one of the housings.

8. The component of claim 4 wherein the different positions are offset in a sagittal plane, by approximately 5 mm with respect to one another.

9. The component of claim 1, wherein said base is provided with an acromio-coracoid bearing flange which extends substantially in a direction perpendicular to a web of said base and said means for adjustably mounting said element including means for securing said element relative to said web.

10. A shoulder prosthesis comprising, a humeral component having a stem from which extends a concave articulation surface member and a glenoid component, said glenoid component including a base adapted to be immobilized on a glenoid cavity of a shoulder and an element including a convex articulation surface adapted to cooperate with the concave articulation surface of the humeral component of the prosthesis, and means for adjustably mounting said element to said base such that said convex articulation surface is selectively positioned with respect to the glenoid cavity.

* * * * *